US012622634B2

(12) United States Patent
Hao et al.

(10) Patent No.: US 12,622,634 B2
(45) Date of Patent: May 12, 2026

(54) DISEASE EARLY DIAGNOSIS SYSTEM BASED ON SEBUM GAS ANALYSIS

(71) Applicant: Huimin Hao, Taiyuan (CN)

(72) Inventors: Huimin Hao, Taiyuan (CN); Huijing Hao, Taiyuan (CN)

( * ) Notice: Subject to any disclaimer, the term of this patent is extended or adjusted under 35 U.S.C. 154(b) by 212 days.

(21) Appl. No.: 18/628,772

(22) Filed: Apr. 7, 2024

(65) Prior Publication Data

US 2024/0268750 A1 Aug. 15, 2024

(30) Foreign Application Priority Data

Apr. 24, 2023 (CN) .......................... 202310448155.0
Apr. 28, 2023 (CN) .......................... 202310479097.8

(51) Int. Cl.
*A61B 5/00* (2006.01)
*G16H 50/20* (2018.01)

(52) U.S. Cl.
CPC .......... *A61B 5/4272* (2013.01); *A61B 5/6814* (2013.01); *A61B 5/6823* (2013.01); *A61B 5/6831* (2013.01); *G16H 50/20* (2018.01); *A61B 2560/0462* (2013.01)

(58) Field of Classification Search
CPC ... A61B 5/4272; A61B 5/6814; A61B 5/6823; A61B 5/6831; A61B 2650/0462; G16H 50/20
USPC ........................................................ 600/300
See application file for complete search history.

(56) References Cited

U.S. PATENT DOCUMENTS

| | | | | |
|---|---|---|---|---|
| 5,945,674 A | * | 8/1999 | Dukor .................. | G01N 21/552 250/341.8 |
| 2004/0100376 A1 | * | 5/2004 | Lye ........................ | A61B 5/411 600/300 |
| 2008/0077037 A1 | * | 3/2008 | Gouma .................. | A61B 5/082 73/23.3 |
| 2009/0326338 A1 | * | 12/2009 | Kobayashi ........... | G01N 33/497 600/300 |
| 2013/0115232 A1 | * | 5/2013 | Ferrara .............. | G01N 33/6893 435/7.92 |
| 2016/0331270 A1 | * | 11/2016 | Yumoto ............... | A61B 5/7278 |
| 2020/0155047 A1 | * | 5/2020 | Rogers ................. | A61B 5/1477 |
| 2021/0349089 A1 | * | 11/2021 | Schulte ............. | G01N 33/6848 |
| 2023/0251243 A1 | * | 8/2023 | Postrel ................ | G01N 33/497 73/23.2 |
| 2024/0003917 A1 | * | 1/2024 | Postrel ................... | G16H 50/20 |
| 2024/0016718 A1 | * | 1/2024 | Maignel ................... | A61K 8/66 |
| 2024/0268750 A1 | * | 8/2024 | Hao ...................... | A61B 5/6823 |

* cited by examiner

*Primary Examiner* — Michael Tomaszewski

(57) ABSTRACT
In response to the difficulty in disease early diagnosis and low diagnostic accuracy in the prior art, a disease early diagnosis system based on sebum gas analysis is provided, which combines a micro-electro-mechanical system, a novel two-dimensional material and a metal surface plasma resonance technology to provide a device for sebum gas collection and infrared spectrum enhancement, which collects human body trace sebum gas and enhances its infrared spectrum by metal plasma resonance, and then the sebum gas metal-plasma-enhanced infrared spectrum is inputted into a disease early diagnosis model for analysis, and ultimately achieved early diagnoses of diseases. The method is a truly non-invasive disease diagnosis method, which is non-invasive, simple, efficient, and has the advantages of no pollution to the environment and no ecological damage.

10 Claims, 4 Drawing Sheets

DISEASE EARLY DIAGNOSIS SYSTEM BASED ON SEBUM GAS ANALYSIS

CROSS REFERENCE OF RELATED APPLICATION

The present invention claims priority under 35 U.S.C. 119(a-d) to CN 202310448155.0, filed Apr. 24, 2023; and CN 202310479097.8, filed Apr. 28, 2023.

BACKGROUND OF THE PRESENT INVENTION

Field of Invention

The present invention relates to a technical field of early diagnosis of diseases, and more particularly to a disease early diagnosis system based on sebum gas analysis.

Description of Related Arts

Material-energy metabolism is one of the characteristics of living organisms, and the products of human metabolism can reflect abnormal changes in the body. When a human has a certain disease, its sweat and sebum metabolic products will emit a specific odor. For example, in diabetic patients, fat is oxidized in the liver to produce ketone bodies, which emit the odor of rotten apples; in patients with chronic nephritis or liver disease, ammonia is emitted due to the retention of urea nitrogen and creatinine in the blood; and in patients with Parkinson's disease (PD), their sebum odor contain perillic aldehyde and other organic gases, which leads to a "musky" body odor; Alzheimer's disease patients emit formaldehyde from their bodies, etc.

The development of many chronic diseases, such as cancer, Parkinson's disease, and Alzheimer's disease, is a slow progression, with some lasting up to 10 years or more before symptoms appear. Taking Parkinson's disease as an example, in 2015, the British Broadcasting Corporation reported that Joy Milne, a nurse, smelled a special odor emanating from her PD-afflicted husband's body 12 years before his signs and symptoms appeared. In 2019, Dr. Tilo Kunath, a renowned Parkinson's disease expert at the University of Edinburgh in the United Kingdom, also researched and confirmed that hippuric acid ($C_9H_9NO_3$), perillic aldehyde ($C_{10}H_{14}O$), eicosane ($C_{20}H_{42}$) and octadecanal ($C_{18}H_{38}$), which are contained in the sebum of the human body, are closely related to PD. If these specific gases can be timely detected at the early stage of the patient's disease, it will provide a basis for the diagnosis and treatment of some diseases, thus realizing the early diagnosis and treatment of disease.

However, it is difficult to detect gases released by the human body. First of all, what forms the body odor is a mixture of gases released from human body sweat, sebum, and other sources, which contains organic volatile components, and its content is very small and difficult to collect. Conventional human sebum gas collection methods collect sebum by wiping gauze on the human skin and then obtain gases through thermal desorption. The collection process is cumbersome and complex, the equipment requirements are very high, and the gas in the desorption process will be mixed with impurities that cannot be removed, which seriously affects the detection accuracy. Secondly, gas chromatography will be inevitably used for sebum gas analysis, which is expensive and complex in operation and greatly increases the threshold and the difficulty of sebum gas analysis. Thirdly, the human sebum gas has a complex composition, which is volatile organic compounds (VOC), wherein conventional VOC detection methods can only test the total concentration of VOC but cannot determine the content of its components.

Conventionally, scholars have begun to pay attention to the relationship between human sebum odor and diseases, trying to diagnose diseases through analyzing the sebum gas. Chen Xing's group developed a portable "electronic nose" combining gas chromatography and surface acoustic wave sensing to analyze human sebum gas, so as to diagnose PD, which exhibited 91.6% specificity and 91.7% sensitivity. Japan's Kinji OHNO team analyzed skin gases and obtained 90.2% analytical accuracy and 85.2% specificity, and concluded that gases on the skin may serve as biomarkers for PD. Nobutaka Hattori's team identified PD after analyzing sebum RNA, age, and gender information. Prof. Hossam Haik's team analyzed the respiratory samples of patients with PD by using chemoresistive sensors and silicon nanowire sensors, as well as gas chromatography-mass spectrometry, and exhibited 76% accuracy, 77% sensitivity, and 73% specificity.

In summary, the analysis of human sebum gas all over the world is still limited by the sebum sampling method, detection instruments, and analytical methods to achieve satisfactory results.

SUMMARY OF THE PRESENT INVENTION

In response to the difficulty in disease early diagnosis and low diagnostic accuracy in the prior art, an object of the present invention is to provide a disease early diagnosis system based on sebum gas analysis, which combines a micro-electro-mechanical system (MEMS), a novel two-dimensional material and a metal surface plasma resonance technology to provide a device for sebum gas collection and infrared spectrum enhancement, which collects human body trace sebum gas and enhances its infrared spectrum by metal plasma resonance. And then, the metal-plasma-enhanced infrared spectrum of sebum gas is inputted into a disease early diagnosis model for analysis if the people with the sebum gas have the disease, and ultimately achieve the early diagnoses of the disease.

Accordingly, in order to accomplish the above objects, the present invention provides:

a disease early diagnosis system based on sebum gas analysis, comprising: a sebum gas collection and infrared spectrum enhancement device, a Fourier Transform Infrared Microscope (FTIR Microscope), a disease early diagnosis model, and a computer; wherein the sebum gas collection and infrared spectrum enhancement device is configured to be attached to a forehead or a back of the human body for 3-5 minutes to collect sebum gas of the human body, and the FTIR Microscope scans a plasma-enhanced infrared spectrum of the sebum gas; then the plasma-enhanced infrared spectrum of the sebum gas is inputted into the disease early diagnosis model installed in the computer; and the disease early diagnosis model analyzes and outputs a diagnostic result of whether a disease is developed.

The sebum gas collection and infrared spectrum enhancement device comprises a fixing strap, a fixing frame provided on the fixing strap, and a nano gas-sensitive core provided in the fixing frame.

The nano gas-sensitive core comprises a substrate made of an optical window material with an infrared transmittance rate of no less than 90%, preferably a $CaF_2$ crystal, so as to ensure that the nano gas-sensitive core is able to transmit infrared light and maintains an infrared transmittance rate of more than 90%. A two-dimensional gas-sensitive material is attached to a top surface of the substrate, so as to adsorb the sebum gases and transmit the infrared light. At the same time, a nano-metallic array is provided on the top surface of the substrate, which generates a surface plasma enhancement effect under infrared light irradiation, thereby enhancing the infrared spectrum of the sebum gas adsorbed on the two-dimensional gas-sensitive material. The top surface of the nano gas-sensitive core is upwardly bonded in the fixing frame, which is 1 mm-2 mm away from a bottom surface of the fixing frame.

The nano-metallic array is a metal array formed by one kind of unit structures, or a metal array formed by multiple kinds of unit structures; a metal adopted is preferably gold or silver, each of the unit structures is a bow-tie structure formed by a pair of isosceles triangles, an elongated rectangular structure, or other structures with a plasma resonance peak at 4.7 $\mu$m-10.5 $\mu$m; a height of the unit structures is 80 nm-120 nm. The above different structures correspond to different plasma resonance peaks, and the plasma resonance of different resonance peaks realizes the infrared spectrum enhancement of different sebum gases. The plasma resonance peaks of the micro-metallic arrays formed by the multiple kinds of unit structures are wider than those of a single unit structure, which can enhance multiple sebum gases infrared spectrum at once.

A breathable protective layer is provided on the fixing frame, which is preferably a breathable protective gauze bonded to an external edge of the fixing frame to prevent the skin from contacting with the nano gas-sensitive core during human testing and to prevent the penetration of impurities.

The nano gas-sensitive core has a monolayer or multiple layers of two-dimensional gas-sensitive material layer is attached to the top surface of the substrate of the nano gas-sensitive core, and the two-dimensional gas-sensitive material is molybdenum disulfide, graphene, carbon nanotubes, or other two-dimensional materials with gas-sensitive properties, so that the nano gas-sensitive core can adsorb sebum gases and ensure the sensitivity and stability of the adsorption of the gases.

Preferably, the fixing strap is an elongated tape, in such a manner that the shape and size of the sebum gas collection and infrared spectrum enhancement device is similar to that of an adhesive bandage for ease of use.

The disease early diagnosis model is built by using neural networks, principal component regression, partial least squares regression, kernel methods, random forests, deep learning, or other effective spectral analysis methods, and creation of the disease early diagnosis model comprises steps of:

1) respectively collecting more than 5000 sebum gas samples from subjects with and without a certain disease by using the sebum gas collection and infrared spectrum enhancement device, and establishing a sample database;

2) if there are less than 2000 sebum gas samples from the subjects with the certain disease in the step 1), expanding the collected sebum gas samples of the subjects with the certain disease through a sample expanding method; and 3) selecting 80% of the sebum gas samples in the sample database for training, and testing with remaining 20% of the sebum gas samples, and optimizing model parameters, thus completing the creation of the disease early diagnosis model.

The sample expanding method of the step 2) comprises specific steps of: after adsorbing sebum gas from a patient, removing a nano gas-sensitive core of the sebum gas collection and infrared spectrum enhancement device, and placing a bottom surface of the nano gas-sensitive core on a heating plate in an airtight heatable gas chamber, wherein a nano-metallic array is located right above a central hole of the heating plate; placing the airtight heatable gas chamber on a sample platform of the FTIR Microscope, so that infrared light of the FTIR Microscope penetrates through upper and lower infrared transmittance windows of the heatable gas chamber as well as the central hole of the heating plate; opening an exhaust valve of the airtight heatable gas chamber, and inputting nitrogen gas of 99.99% purity into the airtight heatable gas chamber to purge for 2-3 minutes; and then rapidly and linearly increasing a temperature of the heating plate in the airtight heatable gas chamber to 100° C. by a heating controller, then increasing the temperature to 110° C., 120° C., 130° C., 140° C., 150° C., 160° C., 170° C., 180° C. and 190° C. with a 10° C. increment each time; inputting 150 sccm nitrogen of 99.99% purity into the airtight heatable gas chamber at starting of the heating controller; obtaining expanded samples of an original sample under corresponding step temperatures, and directly scanning a metal plasma-enhanced infrared spectrum of each of the expanded samples.

The present invention has the following beneficial effects:

1) The sebum gas is collected by the sebum gas collection and infrared spectrum enhancement device, wherein the gas samples are analyzed in laboratory and diagnostic results can be obtained, providing a truly non-invasive disease diagnosis method.

2) The disease early diagnosis system based on the sebum gas analysis can determine whether a disease is developed before symptoms of the disease appear, which provides a basis for disease diagnosis and precise medical treatment.

3) The key component of the disease early diagnosis system based on the sebum gas analysis is the sebum gas collection and infrared spectrum enhancement device, which is similar in shape and size to a conventional adhesive bandage, so that the collection of sebum gas from the human body is as simple and efficient as the operation of the adhesive bandage, and leaving no pollution and ecological damage to the environment.

Element reference: 1—sebum gas collection and infrared spectrum enhancement device, 2—FTIR Microscope, 3—disease early diagnosis model, 4—computer, 5—breathable protective layer, 6—fixing frame, 7—nano gas-sensitive core, 8—fixing strap, 9—nano-metallic array, 10—two-dimensional material, 11—substrate.

DETAILED DESCRIPTION OF THE PREFERRED EMBODIMENT

Referring to the accompanying drawings, the present invention will be further illustrated as follows.

Figure 1:
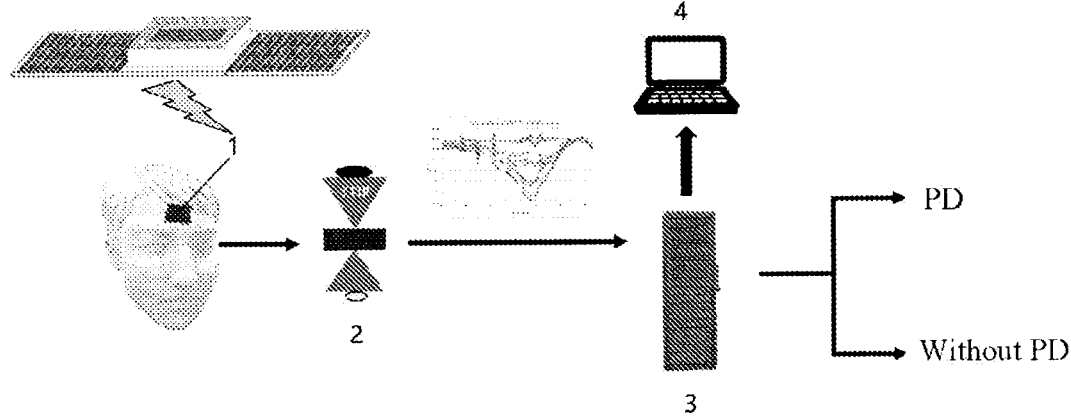
FIG. 1 is a perspective view of the components of a disease early diagnosis system based on sebum gas analysis according to the present invention.

Referring to FIG. 1, a disease early diagnosis system based on sebum gas analysis, comprising: a sebum gas collection and infrared spectrum enhancement device 1, a FTIR Microscope 2, a disease early diagnosis model 3, and a computer 4; wherein the sebum gas collection and infrared spectrum enhancement device 1 is configured to be attached to a forehead or a back of the human body for 3-5 minutes, and the FTIR Microscope 2 scans a plasma-enhanced infrared spectrum of the sebum gas; then the plasma-enhanced infrared spectrum of the sebum gas is inputted into the disease early diagnosis model 3 installed in the computer 4; and the disease early diagnosis model analyzes and outputs a diagnostic result of whether a disease is developed.

Figure 2:
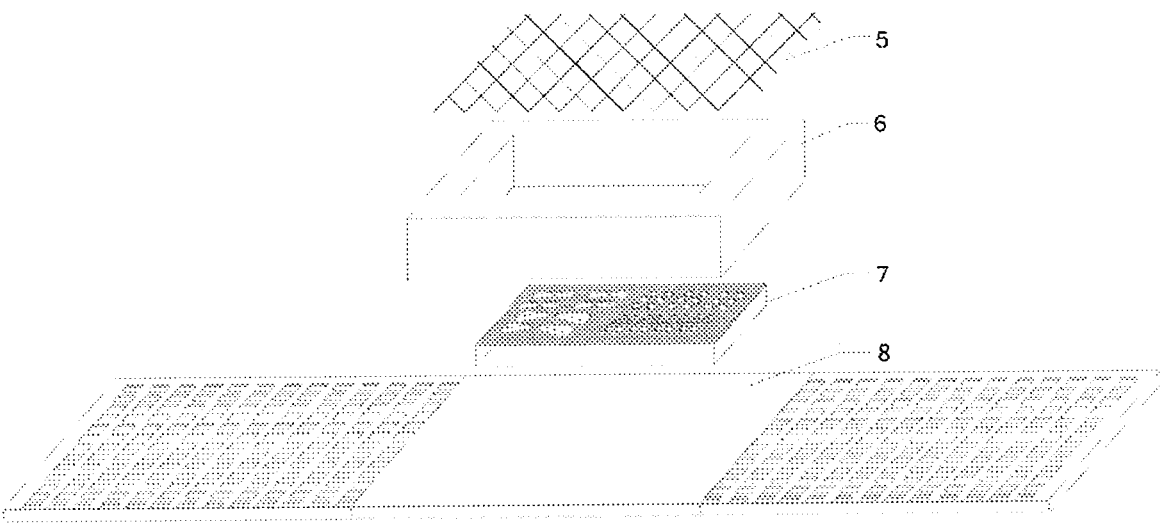
FIG. 2 is an exploded view of a sebum gas collection and infrared spectrum enhancement device of the present invention.

Referring to FIG. 2, the sebum gas collection and infrared spectrum enhancement device 1 comprises a fixing strap 8, a fixing frame 6 provided on the fixing strap 8, and a nano gas-sensitive core 7 provided in the fixing frame 6. A breathable protective layer 5 is provided on the fixing frame 6, which is a breathable protective gauze bonded to an external edge of the fixing frame.

Figure 3:
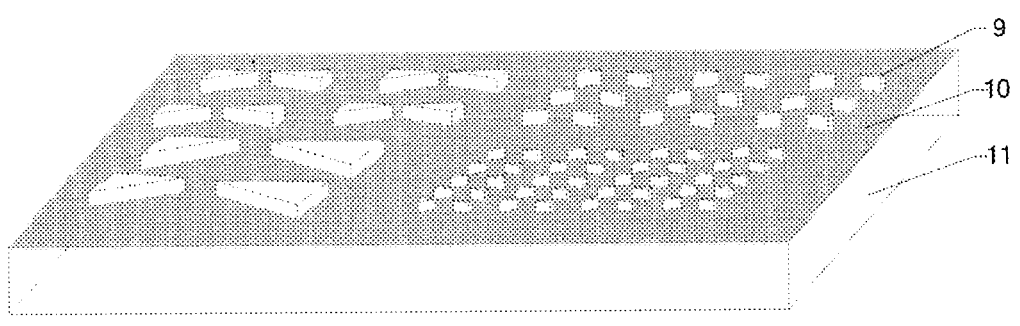
FIG. 3 is a three-dimensional structural view of a nano gas-sensitive core of the sebum gas collection and infrared spectrum enhancement device of the present invention.

Referring to FIG. 3, the nano gas-sensitive core 7 comprises a substrate 11 made of an optical window material with an infrared transmittance rate of no less than 90%, wherein a monolayer or multiple layers of two-dimensional gas-sensitive material 10 is attached to a top surface of the substrate 11, and a nano-metallic array 9 is provided on the top surface of the substrate 11. The nano-metallic array 9 is a metal array formed by one kind of unit structures, or a metal array formed by multiple kinds of unit structures; a metal adopted is preferably gold or silver, each of the unit structures is a bow-tie structure formed by a pair of isosceles triangles, an elongated rectangular structure, or other structures with a plasma resonance peak at 4.7 μm-10.5 μm; a height of the unit structures is 80 nm-120 nm.

The disease early diagnosis model 3 is built by using neural networks, principal component regression, partial least squares regression, kernel methods, random forests, deep learning, or other effective spectral analysis methods.

Embodiment 1

Referring to FIG. 1, the embodiment 1 takes the diagnosis of Parkinson's disease (PD) as an example, and provides a disease early diagnosis system based on sebum gas analysis, comprising: a sebum gas collection and infrared spectrum enhancement device 1, a FTIR Microscope 2, a disease early diagnosis model 3, and a computer 4.

Referring to FIG. 2, the sebum gas collection and infrared spectrum enhancement device 1 comprises a fixing strap 8, a fixing frame 6 provided on the fixing strap 8, and a nano gas-sensitive core 7 provided in the fixing frame 6. The fixing frame 6 is a square hollow structure with a height of 6 mm and a wall thickness of 2 mm, and internal dimensions thereof are 5.5 mm×5.5 mm. The fixing frame 6 is provided with the breathable protective layer 5, which is a 9.5 mm×9.5 mm square sterile breathable gauze. The edges of the breathable protective layer 5 are aligned with external edges of the fixing frame 6 and bonded to a top surface of the fixing frame 6. The fixing strap 8 is an elongated tape, wherein both ends of an upper surface of the elongated tape are adhesive, while a middle portion of the upper surface as well as a lower surface of the elongated tape are not adhesive. The middle portion of the upper surface that is not adhesive is a square of 10 mm×10 mm. The bottom surface of the fixing frame 6 is adhered to the middle portion of the upper surface of the fixing strap 8 that is not adhesive.

Referring to FIG. 3, the nano gas-sensitive core 7 comprises a substrate 11 made of an optical window material with an infrared transmittance rate of no less than 90%, wherein a monolayer or multiple layers of two-dimensional gas-sensitive material 10 is attached to a top surface of the substrate 11, and a nano-metallic array 9 is provided on the top surface of the substrate 11.

According to the embodiment 1, the substrate 11 of the nano gas-sensitive core 7 is a double-side-polished square $CaF_2$ crystal with a length of 5 mm, a width of 5 mm and a thick of 0.5 mm. The two-dimensional gas-sensitive material is a single layer of molybdenum disulfide. The nano-metallic array 9 is processed on $CaF_2$ by electron beam lithography. A top surface of the nano-gas-sensitive core 7 is upwardly bonded and fixed inside the fixing frame 6, which is 1.5 mm away from a bottom surface of the fixing frame 6.

Figure 4:
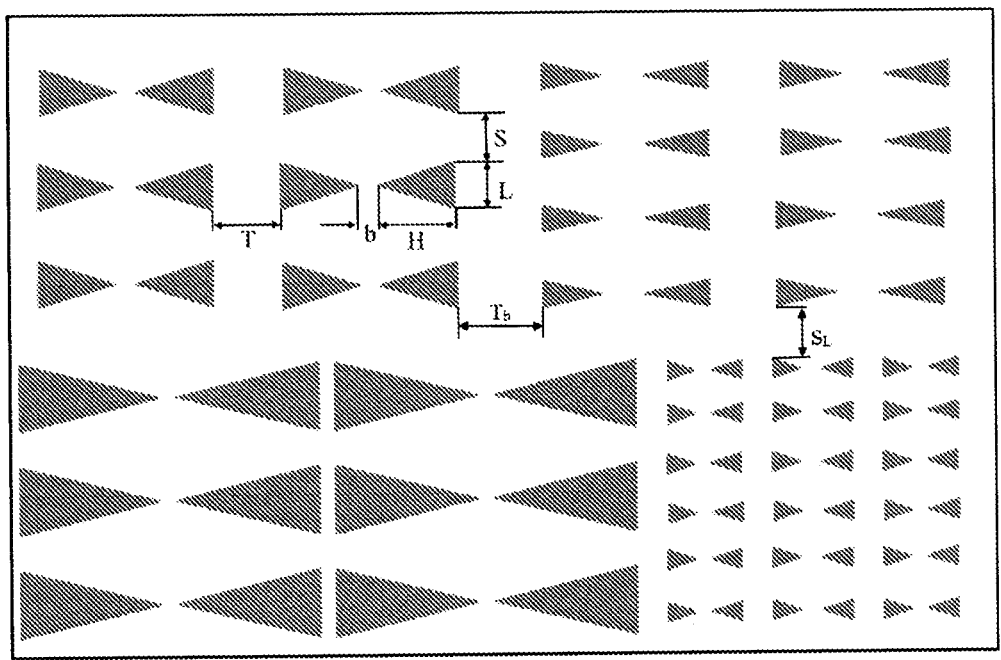
FIG. 4 is a perspective view of a nano-metallic array according to an embodiment 1 of the present invention.

Based on the infrared spectra of four PD-related organic gases (hippuric acid, perillic aldehyde, eicosane and octadecanal) reported by Dr. Tilo Kunath, the embodiment 1 determined that the main infrared spectrum peaks of the gas mixture formed by hippuric acid, perillic aldehyde, eicosane and octadecanal appear between 5.85 μm-6.18 μm, and the nano-metallic array 9 is prepared correspondingly. As shown in FIG. 4, the nano-metallic array 9 consists of four different bow-tie-shaped unit structures. A metal adopted is gold with a thickness of 80 nm, lengths L of bottom edges of the triangles in the bow-tie are 80 nm, 90 nm, 100 nm, and 116 nm respectively; heights H are 100 nm, 120 nm, 135 nm, and 150 nm respectively, vertex spacings b between two triangles are 46 nm, 75 nm, 95 nm and 120 nm respectively, transverse spacings T of bow-ties inside the four arrays are 60 nm, 100 nm, 300 nm and 500 nm respectively, longitudinal spacings S of bow-ties inside the four arrays are 1 μm, transverse spacings $T_h$ between the four bow-tie arrays are 600 nm, and longitudinal spacings $S_L$ between the four bow-tie arrays are 2 μm.

Figure 5:
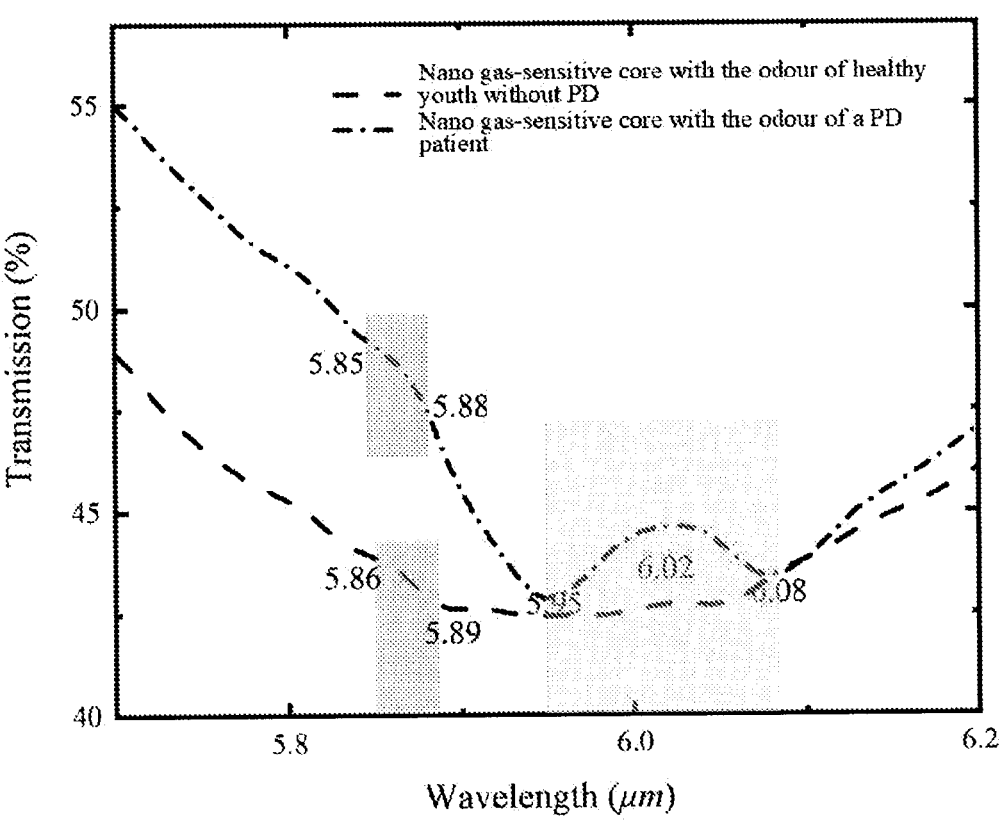
FIG. 5 illustrates metal plasma-enhanced infrared spectrum comparison of sebum gas between PD patients and healthy youths without PD according to the embodiment 1 of the present invention.

Distinguishing from the conventional narrow-peak metal plasma-enhanced spectra obtain by single unit structure, the nano-metallic array according to the embodiment 1 obtained a broad-peak metal plasma-enhanced infrared spectrum of 5.88 μm-6.09 μm. As shown in FIG. 5, after adsorbing the sebum gas of a PD patient, spectrum enhancement occurs between 5.95 μm-6.08 μm, and a slight sub-peak enhancement occurs between 5.85 μm-5.88 μm. After adsorbing the sebum gas of a healthy youth without PD, only a slight spectrum enhancement can be observed between 5.86 μm-5.89 μm, while no spectrum enhancement occurs between 5.95 μm-6.08 μm.

Figure 6:
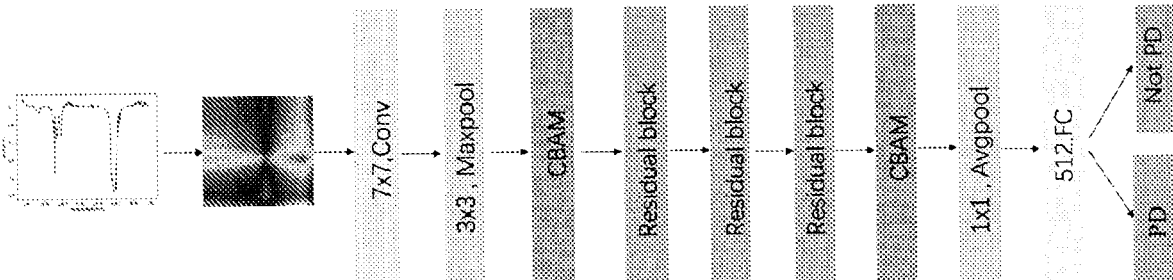
FIG. 6 is a network framework diagram of GADF-coupled CBAM-CNN deep learning according to the embodiment 1 of the present invention.

The disease early diagnosis model 3 was built for early diagnosis of PD. Composition of sebum gas is complex, and there is cross-sensitivity between the infrared spectra of PD patients and those without PD (5.86 μm-5.88 μm in FIG. 5). Therefore, in order to eliminate the cross-sensitivity of the spectra and further extract the feature information from the spectra, the disease early diagnosis model of the embodiment 1 was built based on 12188 sebum gas samples using a Gram's angular difference field (GADF) coupled with a convolutional block attention module-convolutional neural network (CBAM-CNN) as shown in FIG. 6, comprising steps of: transforming spectral data into a two-dimensional color image by GADF, and then performing convolution (7×7, Conv), maximum pooling (3×3, Maxpool), CBAM, residual block, CBAM, average pooling (1×1, Avgpool), and fully connected layer (512, FC), and finally classifying the spectral data. The 12188 sebum gas samples include the samples directly collected from 1862 people using the sebum gas collection and infrared spectrum enhancement device 1 and expanded samples of the partial directly collected samples. The 12188 sebum gas samples include a total of 6088 sebum gas samples from patients with diagnosed PD and 6100 sebum gas samples from people without PD. The 1862 people included 526 patients with diagnosed PD and 1336 people without PD, wherein the 526 PD patients were 393 male patients and 133 female patients, with patients' ages ranging from 56-83 years old and disease duration from 0.5-8 years. The 1336 people without PD included 720 males and 616 females, with ages ranging from 7-35 years old. Each of the 526 patients with PD provided at least 20 different sebum gas samples, and the 20 different samples were sampled on 2 days, which were 1 hour before and after breakfast, lunch and dinner; 1 hour after morning and evening medication; as well as before and after skin cleansing; and also included samples taken after aerobic exercise in individual patients and expanded samples for some of the samples. Each of the 1336 people without PD provided at least 6 different sebum gas samples taken on 2 days, which were 1 hour before and after breakfast and dinner, as well as before and after skin cleansing. Metal plasma-enhanced infrared spectra of all 12188 sebum gas samples were scanned with the FTIR Microscope 2, and were transformed into two-dimensional color images by a GADF method. 4870 and 4880 GADF-transformed two-dimensional color images obtained from 6088 PD patients and 6100 people without PD were randomly selected, respectively, for training the CBAM-CNN deep learning network. The trained CBAM-CNN deep learning network was tested with the remaining 1218 and 1220 GADF-transformed two-dimensional color images and the model parameters were optimized, so as to finally complete the creation of the PD early diagnosis model.

Figure 7:
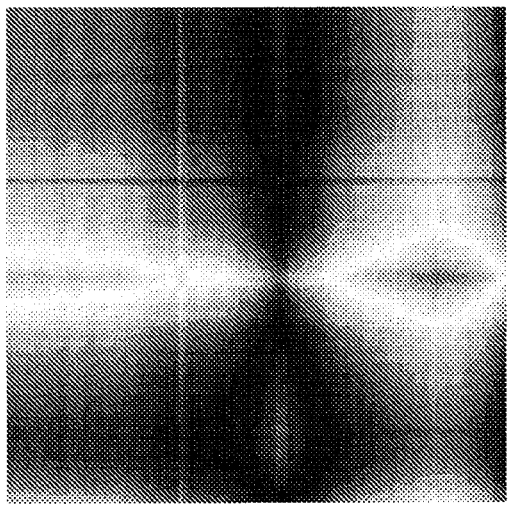
FIG. 7 is a two-dimensional image of a GADF-transformed infrared spectrum of PD patient sebum gas according to the present invention.
Figure 8:
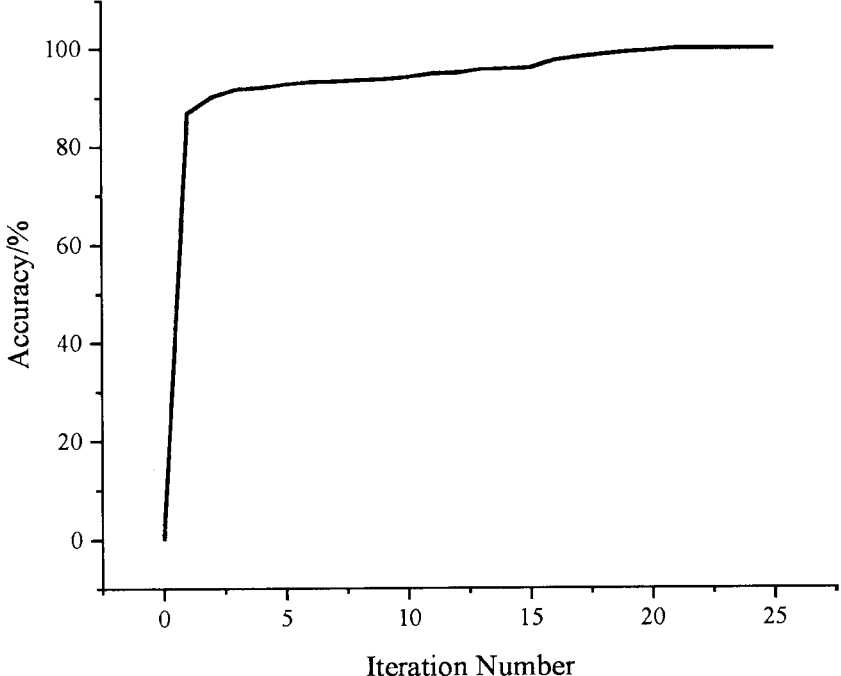
FIG. 8 illustrates iterative processes of CBAM-CNN model training according to the embodiment 1 of the present invention.

As an example, FIG. 7 illustrates a two-dimensional image of a GADF-transformed sebum gas sample obtained from a PD patient. When training parameters of the CBAM-CNN deep learning network were: batch size=16, optimizer set to adam, learning rate=0.0001, and training epochs=25, the training accuracy of the model reached 99.1%, as shown in FIG. 8, and the test accuracy on 2438 test samples was 98.2%.

The expanded samples were obtained by a sample expanding method for the samples comprises specific steps of: after adsorbing sebum gas from a patient, removing a nano gas-sensitive core of the sebum gas collection and infrared spectrum enhancement device, and placing a bottom surface of the nano gas-sensitive core on a heating plate in an airtight heatable gas chamber, wherein a nano-metallic array is located right above a central hole of the heating plate; placing the airtight heatable gas chamber on a sample platform of the FTIR Microscope, so that infrared light of the FTIR Microscope penetrates through upper and lower infrared transmittance windows of the heatable gas chamber as well as the central hole of the heating plate; opening an exhaust valve of the airtight heatable gas chamber, and inputting nitrogen gas of 99.99% purity into the airtight heatable gas chamber to purge for 2-3 minutes; and then rapidly and linearly increasing a temperature of the heating plate in the airtight heatable gas chamber to 100° C. by a heating controller, then increasing the temperature to 110° C., 120° C., 130° C., 140° C., 150° C., 160° C., 170° C., 180° C. and 190° C. with a 10° C. increment each time; continuously inputting nitrogen of 99.99% purity and a flow rate of 150 sccm into the airtight heatable gas chamber when the heating controller was activated; obtaining expanded samples of an original sample under corresponding step temperatures, and directly scanning a metal plasma-enhanced infrared spectrum of each of the expanded samples.

During sebum gas collection, the breathable protective layer 5 of the sebum gas collection and infrared spectrum enhancement device 1 is attached to the back of a diagnosed person, and the sebum gas collection and infrared spectrum enhancement device 1 is fixed to the human body through the fixing strap 8, and should be kept there for 5 minutes to complete the sebum gas collection of the diagnosed person. Then the nano gas-sensitive core 7 of the sebum gas collection and infrared spectrum enhancement device 1 is taken out, and the nano gas-sensitive core 7 is placed on the sample holder of FTIR Microscope 2 with the top surface upward. The infrared spectrum of the nano gas-sensitive core adsorbed with the sebum gas of the diagnosed person is scanned with the FTIR Microscope 2, and the scanned spectrum is input into the PD early diagnosis model. The PD early diagnosis model outputs a classification result of whether or not a person suffers from PD, thereby realizing the early diagnosis of PD.

What is claimed is:

1. A disease early diagnosis system based on sebum gas analysis, comprising: a sebum gas collection and infrared spectrum enhancement device, a FTIR (Fourier Transform Infrared) Microscope, a disease early diagnosis model, and a computer; wherein the sebum gas collection and infrared spectrum enhancement device is configured to be attached to a forehead or a back of the human body for 3-5 minutes to collect sebum gas of the human body, and the FTIR Microscope scans a plasma-enhanced infrared spectrum of the sebum gas; then the plasma-enhanced infrared spectrum of the sebum gas is inputted into the disease early diagnosis model installed in the computer; and the disease early diagnosis model analyzes and outputs a diagnostic result of whether a disease is developed.

2. The disease early diagnosis system, as recited in claim 1, wherein the sebum gas collection and infrared spectrum enhancement device comprises a fixing strap, a fixing frame provided on the fixing strap, and a nano gas-sensitive core provided in the fixing frame.

3. The disease early diagnosis system, as recited in claim 2, wherein the nano gas-sensitive core comprises a substrate made of an optical window material with an infrared transmittance rate of no less than 90%, wherein a monolayer or multiple layers of a two-dimensional gas-sensitive material is attached to a top surface of the substrate, and a nano-metallic array is provided on the top surface of the substrate.

4. The disease early diagnosis system, as recited in claim 3, wherein the substrate is made of a CaF$_2$ crystal.

5. The disease early diagnosis system, as recited in claim 3, wherein the nano-metallic array is a metal array formed by one kind of unit structures, or a metal array formed by multiple kinds of unit structures; a metal adopted is gold or silver, each of the unit structures is a bow-tie structure formed by a pair of isosceles triangles, an elongated rectangular structure, or other structures with a plasma resonance peak at 4.7 μm-10.5 μm; a height of the unit structures is 80 nm-120 nm.

6. The disease early diagnosis system, as recited in claim 2, wherein a breathable protective layer is provided on the fixing frame, which is a breathable protective gauze bonded to an external edge of the fixing frame.

7. The disease early diagnosis system, as recited in claim 3, wherein the two-dimensional gas-sensitive material attached to the top surface of the substrate of the nano gas-sensitive core is molybdenum disulfide, graphene, carbon nanotubes, or other two-dimensional materials with gas-sensitive properties.

8. The disease early diagnosis system, as recited in claim 2, wherein the fixing strap is an elongated tape.

9. The disease early diagnosis system, as recited in claim 1, wherein the disease early diagnosis model is built by using neural networks, principal component regression, partial least squares regression, kernel methods, random forests, deep learning, or other effective spectral analysis methods, and creation of the disease early diagnosis model comprises steps of:

1) respectively collecting more than 5000 sebum gas samples from subjects with and without a certain disease by using the sebum gas collection and infrared spectrum enhancement device, and establishing a sample database;

2) if there are less than 2000 sebum gas samples from the subjects with the certain disease in the step 1), expanding the collected sebum gas samples of the subjects with the certain disease through a sample expanding method; and 3) selecting 80% of the sebum gas samples in the sample database for training, and testing with remaining 20% of the sebum gas samples, and optimizing model parameters, thus completing the creation of the disease early diagnosis model.

10. The disease early diagnosis system, as recited in claim 9, wherein the sample expanding method of the step 2) comprises specific steps of: after adsorbing sebum gas from a patient, removing a nano gas-sensitive core of the sebum gas collection and infrared spectrum enhancement device, and placing a bottom surface of the nano gas-sensitive core on a heating plate in an airtight heatable gas chamber, wherein a nano-metallic array is located right above a central hole of the heating plate; placing the airtight heatable gas chamber on a sample platform of the FTIR Microscope, so that infrared light of the FTIR Microscope penetrates through upper and lower infrared transmittance windows of the heatable gas chamber as well as the central hole of the heating plate; opening an exhaust valve of the airtight heatable gas chamber, and inputting nitrogen gas of 99.99% purity into the airtight heatable gas chamber to purge for 2-3 minutes; and then rapidly and linearly increasing a temperature of the heating plate in the airtight heatable gas chamber to 100° C. by a heating controller, then increasing the temperature to 110° C., 120° C., 130° C., 140° C., 150° C., 160° C., 170° C., 180° C. and 190° C. with a 10° C. increment each time; inputting 150 sccm nitrogen of 99.99% purity into the airtight heatable gas chamber at starting of the heating controller; obtaining expanded samples of an original sample under corresponding step temperatures, and directly scanning a metal plasma-enhanced infrared spectrum of each of the expanded samples.

* * * * *